United States Patent [19]

Sobel et al.

[11] 4,052,216

[45] Oct. 4, 1977

[54] COLOR PHOTOGRAPHIC MATERIAL CONTAINING A HYDROXYINDANE

[75] Inventors: Johannes Sobel, Leverkusen; Alfons Klein, Dusseldorf; Fritz Nittel, Leverkusen; Karlfried Wedemeyer, Cologne, all of Germany

[73] Assignee: Agfa-Gevaert Aktiengesellschaft, Leverkusen, Germany

[21] Appl. No.: 693,942

[22] Filed: June 8, 1976

[30] Foreign Application Priority Data

June 13, 1975 Germany .................................. 2526468

[51] Int. Cl.$^2$ ...................... G03C 1/84; G03C 1/40; G03C 1/02
[52] U.S. Cl. ............................. 96/84 UV; 96/56; 96/100 R; 96/114.5
[58] Field of Search ............. 96/56, 100, 84 UV, 114.5

[56] References Cited

U.S. PATENT DOCUMENTS

| | | | |
|---|---|---|---|
| 3,573,050 | 3/1971 | Brannock et al. | 96/84 UV |
| 3,574,627 | 4/1971 | Stern et al. | 96/56 |
| 3,689,271 | 9/1972 | Nittel et al. | 96/84 UV |
| 3,887,378 | 6/1975 | Klein et al. | 96/114.6 |

*Primary Examiner*—J. Travis Brown
*Attorney, Agent, or Firm*—Connolly and Hutz

[57] ABSTRACT

A color photographic recording material is provided containing at least one dye image or a color coupler for the production of a dye image and the material contains in at least one hydrophilic layer a hydroxyindane as defined hereinafter to reduce the fading of the image dye on exposure to UV or visible light.

3 Claims, No Drawings

COLOR PHOTOGRAPHIC MATERIAL CONTAINING A HYDROXYINDANE

The invention relates to a colour photographic recording material containing colour couplers and, in addition, at least one hydroxy indane derivative as a means for preventing the bleaching of the dye images formed from the colour couplers in chromogenic development.

Normally to produce cyan dye images, phenolic couplers, i.e. phenols and naphthols, are used; for the production of magenta dye images, pyrazolone, indazolone or cyanacetyl couplers are used and, for the production of yellow dye images, open chained ketomethylene compounds, e.g. acylacetamide or dibenzoylmethane couplers are used.

In known colour photographic processes, the dye forming couplers are either used in a developer solution or they are incorporated into the light-sensitive photographic emulsion layers or other dye forming layers, so that during development they can react with the oxidation products of colour developer compounds while forming dyes.

The dye images produced in the manner described above are, as is known, not altogther stable against the effects of ultraviolet radiation or visible light, so that they gradually fade if exposed for a long time.

To reduce or substantially to obviate this disadvantage attempts have been made, for example, to incorporate an ultraviolet absorption means into the colour photography material, so as to reduce the harmful effects of ultraviolet radiation. The use of an ultraviolet absorber however in no way prevents the bleaching of the colour image, through the effects of visible light, so that the improvement of the dye stability against the effects of light by the use of ultraviolet absorbers is limited and still not wholly accomplished.

It has now been found, that the lightproof qualitites of colour images produced by photographic means can be considerably improved by the use of hydroxy indane derivatives of the following formula:

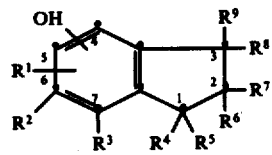

in which
R$^1$ represents hydrogen, a straight or branched chain alkyl group with preferably up to 12 carbon atoms, such as a methyl, ethyl, propyl, butyl, octyl or nonyl group; a cycloalkyl group, such as a cyclopentyl or cyclohexyl group, an aralkyl group, such as a benzyl group or a further hydroxy indane radical bonded by —S—, —SO$_2$—, —O— or a straight or branched chain alkylene bridge of the above formula, in particular an alkylene bridge of the following formula

R$^2$ and R$^3$ may be the same or different and represent hydrogen, halogen, in particular chlorine, —NO$_2$, carboxyl, straight or branched chain alkyl, with preferably up to 12 carbon atoms, cycloalkyl such as cyclopentyl or cyclohexyl, aralkyl such as benzyl, or aryl such as phenyl, where the alkyl, cycloalkyl, aryl or aryl radicals may contain further substituents or R$^2$ and R$^3$ may together represent the carbon atoms necessary to complete a condensed carbocyclic ring which may be substituted;

R$^4$ and R$^5$ which may be the same or different and represent hydrogen, straight or branched chain alkyl with preferably up to 6 carbon atoms, cycloalkyl such as cyclopentyl or cyclohexyl, aryl such as phenyl, which radicals mentioned may contain further substituents; or R$^4$ and R$^5$ may together represent the ring members required to complete a cycloaliphatic, preferably 5- or 6-membered, ring;

R$^6$ and R$^7$ which may be the same or different and represent hydrogen, straight or branched chain alkyl with preferably up to 6 carbon atoms, cycloalkyl such as cyclopentyl or cyclohexyl, aralkyl such as benzyl, or aryl such as phenyl, where R$^6$ and R$^7$ can optionally contain further substituents; in addition R$^6$ and R$^7$ can represent the ring members required to complete cycloaliphatic ring with preferably 5 or 6 ring members;

R$^8$ and R$^9$ which may be the same or different and have the same meanings as R$^6$ and R$^7$; when R$^8$ and R$^9$ together represent the radical necessary to complete a 5- or 6-membered carboxcyclic ring, this annellated radical can contain a hydroxyl substituted benzo ring, so that a dihydroxyspiro-bis-indane is present;

R$^{10}$ and R$^{11}$ which may be the same or different and represent hydrogen, a straight or branched chain alkyl group with preferably up to 9 carbon atoms or R$^{10}$ and R$^{11}$ together form the ring members required to complete a cycloaliphatic ring with preferably 5 or 6 ring members.

It is therefore an object of the present invention to provide a photographic material, which comprises at least one hydrophilic binder layer, which layer contains a dye image or a colour coupler for the production of a dye image which material contains in addition a hydroxyindane derivative of the above formula.

The photographic material of the present invention may further contain at least one silver halide emulsion layer which layer may be exposed, developed and fixed and may contain the above mentioned dye image in the said emulsion layer or in a hydrophilic layer adjacent thereto.

Particularly suitable are those hydroxy indanes of the above formula in which the hydroxyl group is in the 5-position and R$^1$ in the 6-position represents hydrogen, alkyl, in particular isopropyl, tert.-butyl, tert.-octyl, isononyl or cycloalkyl, or a further hydroxy indane radical, bonded by a bridge member, of the following formula:

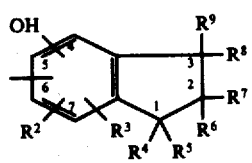

where the radicals R² to R⁹ have the above specified meanings.
Examples of the compounds used according to the invention for improving lightproof qualitites are provided by hydroxy indanes of the following formulae:
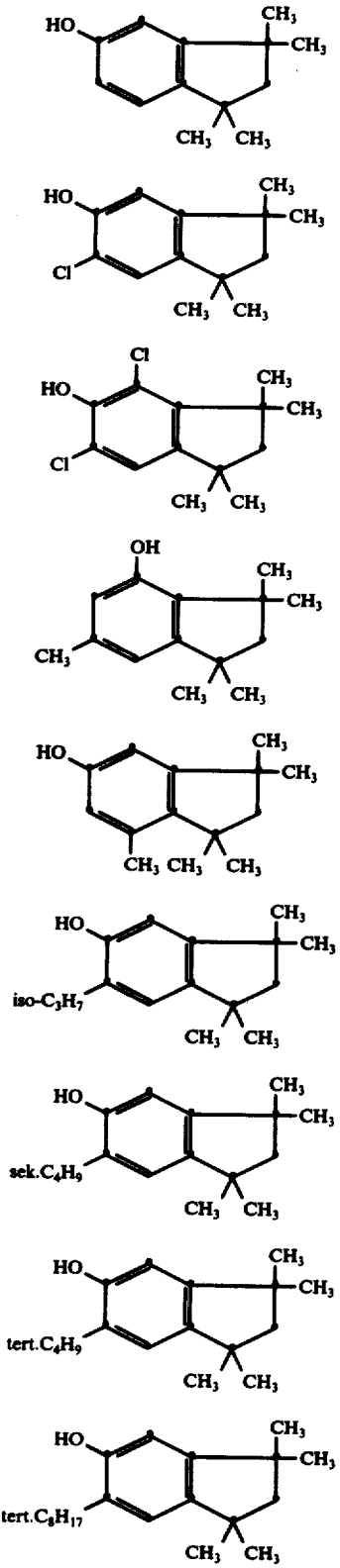
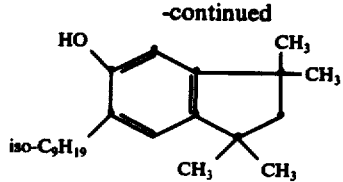
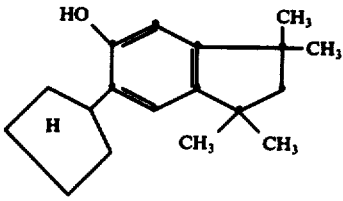
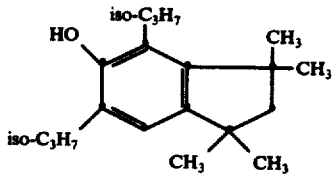
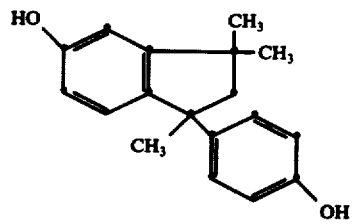
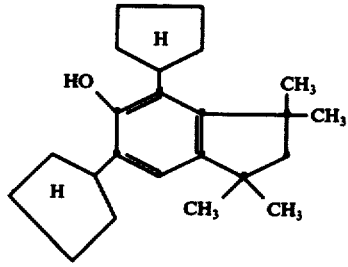
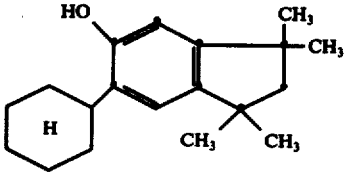
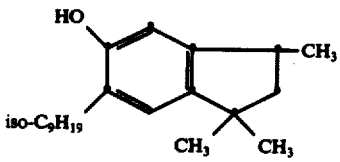

-continued

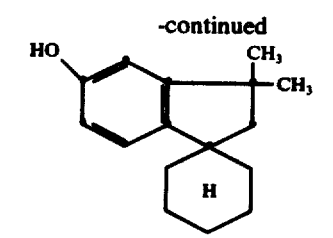

19.

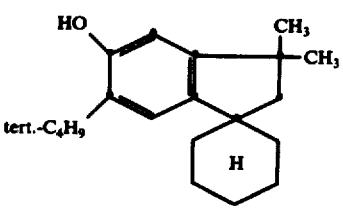

20.

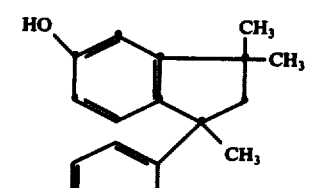

21.

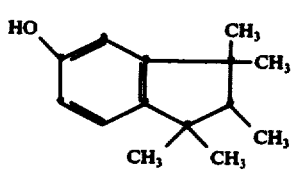

22.

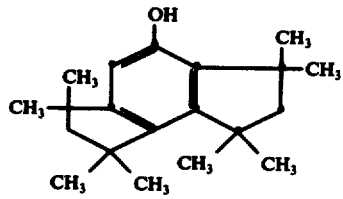

23.

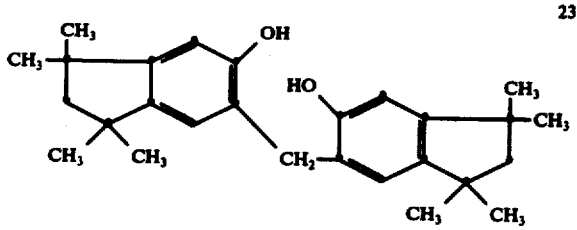

24.

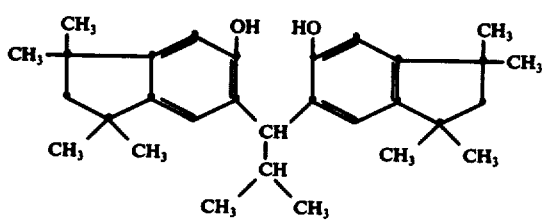

25.

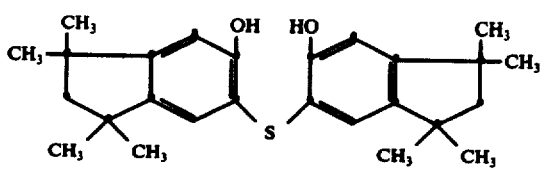

26.

-continued

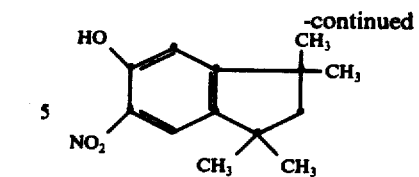

27.

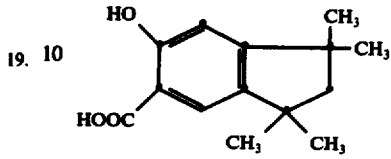

28.

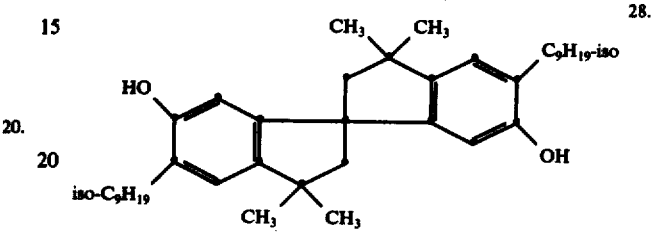

29.

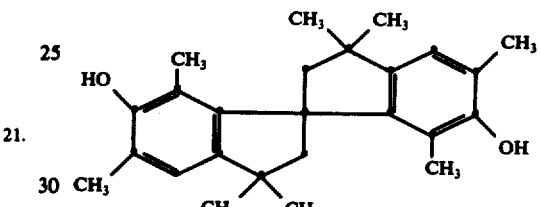

30.

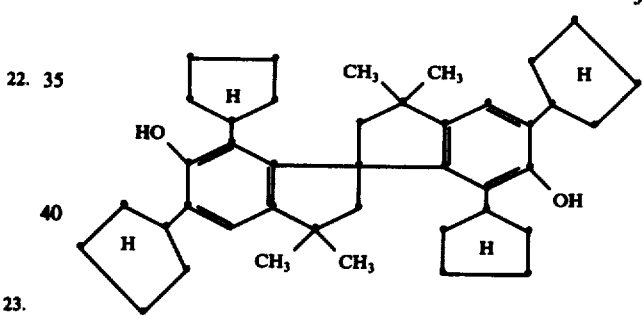

The hydroxy indanes to be used in the manner according to the invention are known from British Pat. No. 1 398 375, and as described therein are obtained by the reaction of alkyl phenols with olefins, in which at least one double bonded carbon atom has exclusively carbon bonds, in the presence of acid catalysts at temperatures between 100° and 350° C. In this process the desired substituents can be already present in the alkyl phenol or added later to the hydroxy indane. The dihydroxy-spiro-bisindanes to be used in the manner according to the invention are known and can be produced according to J.chem. Soc. 1962, pages 415–417.

The production process is illustrated with reference to the following examples.

Production of
1,1,3,3-tetramethyl-6-isononyl5-hydroxy-indane
(compound No. 10).

760 g 1,1,3,3-tetramethyl-5-hydroxy-indane, 2000 g tripropylene and 10 ml borofluoride-etherate are stirred for 1.5 hours at 20° to 25° C whilst being cooled with water. Then 30 g white-lime hydrate are added and stirred for 1 hour at 50° C. The reaction mixture is removed from the lime and the excess tripropylene is distilled off in a water stream vacuum to an absorbtion temperature of 150° C. The residue consists of 1268 g 1,1,3,3-tetramethyl-6-isononyl-5-hydroxy-indane in the form of a yellowish viscous oil.

Production of 5-hydroxy1,1,3,3-tetramethyl-4, 6-di cyclopentyll-indane (compound No. 14).

515 g cyclopentane are dripped into 665 g (3.5 mol) 5-hydroxy-1,1,3,3-tetramethyl-indane and 66 g p-toluenesulphonic acid while stirring at 120° C over 3 to 4 hours. The mixture is left to react for 2 hours at 120° C. After adding 2.4 liters toluene the catalyst is washed out with diluted sodium hydrogen carbonate solution at 70 to 80° C. After the solvent has been distilled off there remains a crude alkylate, from which by re-crystallisation from isopropanol, 610 g of pure 5-hydroxy-1,1,3,3-tetramethyl-4, 6-dicyclopentyl-indane with a melting point of 145 to 146° C, can be obtained.

The compounds of formula (I) are effective stabilisers for the improvement of the light stability of indophenol, indoaniline and azomethine dyes produced by chromogenic development, in particular of dye images, which are obtained by chromogenic development of 5-pyrazolone colour couplers.

The compounds used according to the invention for preventing bleaching can be used in combination with a ultraviolet absorber, and in this way the lightproof quality of the colour image can be improved still further. Examples of suitable ultraviolet absorbers are provided by compounds based on benzophenone; acrylonitrile; thiazolidone; benzotrizole; stilbene; oxazole; thiazole and imidazole.

The compounds according to the invention are basically colourless; therefore they do not detract from the image whites and do not have any negative influence on colour development or on other photograpic additives.

Two or more of the hydroxy indanes can optionally be used. The hydroxy indanes can also optionally be used together with other known stabilisers, anti-stain agents, for example with hydroquinones having groups which render them diffusion fast and phenolic antioxidation agents.

The concentration of the hydroxy indanes in the photographic layers may vary widely and, in general depends on the improvement in stability which is required. It has proved suitable to use the stabilisers in quantities of from 0.2 to about 2 parts by weight per 1 part by weight of colour coupler. Preferably about 0.5 to 1 parts by weight of stabiliser are used per 1 part by weight of coupler.

The hydroxy indanes used according to the invention are particularly used in hydrophilic colloidal binder layers which also contain the colour coupler for the production of the colour image. These can be silver halide emulsion layers or non-light sensitive binder layers, which are adjacent. The hydroxy indanes used according to the invention are emulsified in known manner, e.g. by mixing a solution of these compounds in a low boiling solvent directly with the silver halide emulsion or the coating solution for the layer containing the coupler of first of all mixing them with an aqueous gelatine solution, the organic solvent then being allowed to evaporate. The hydroxy indanes can usefully be used together with the colour coupler.

A gelatine emulsion of the compounds in question obtained in this way is subsequently mixed with the silver halide emulsion or the coating solution containing the colour coupler. Optionally one can also use so-called coupler solvents or oil formers additionally for the emulsification of the hydroxy indanes; these are in general organic compounds with a higher boiling point, which enclose the non-diffusing colour couplers which are to be emulsified in the silver halide emulsions in the form of oily drops. Reference should be made in this connection, for example, to U.S. Pat. Nos. 2,322,027; 3,689,271; 3,764,336 and 3,765,897.

It has surprisingly been found that, with the combined use of the hydroxy indane derivatives of the present invention with oil forming agents, which are base on alpha-substituted succinic acid derivatives with at least one free carboxyl group, significantly improved image whites are obtained, compared with the use of conventional oil forming agents, e.g. dibutylphthalate. The alpha-substituted succinic acid derivatives with at least one free carboxyl group are compounds of the general formula:

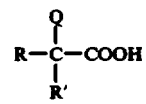

in which
R represents a saturated or olefinically unsaturated, aliphatic hydrocarbon group with 1 to 18 carbon atoms, which may be substituted,
R' represents hydrogen or a saturated or olefinically unsaturated aliphatic hydrocarbon group with 1 to 18 carbon atoms which may be substituted;
Q represents —COX or —CH$_2$COX, in which X represents hydrogen, a hydroxy or alkoxy group; the group —O-Alkylene-[O-Alkylene]$_n$-O-alkyl, in which $n = 0$–10, or an optionally substituted amino, hydrazino or hydroxylamino group.

These oil forming agents are, for example, described in U.S. Pat. No. 3,689,271.

When the hydroxy indanes used according to the invention are used in a layer containing a colour coupler, it is useful to produce an emulsion of the colour coupler and hydroxy indane, which is then added to the coating solution for the particular layer. Such an emulsion product does not necessarily have to contain an additional oil forming agent. The hydroxy indanes used according to the invention are in some cases themselves suitable as oil forming agents, so that in themselves they combine the functions of dye stabilising agent and oil forming agent. It is clear that in this way there results a lower loading of the layer which has a favourable effect on the layer thickness.

I. Production of the coupler containing emulsions

1. Magenta Coupler Emulsion 5 g sulphosuccinic acid-bis-(2-ethyl-hexyl)-ester followed by 50 g magenta coupler of the following constitution are dissolved in 100 g diethylcarbonate at 40° C

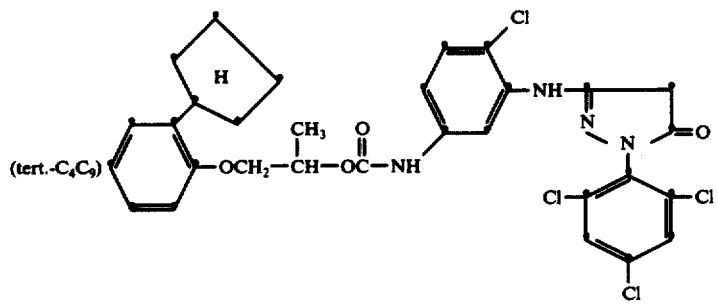

Subsequently 50 g of a 50% solution of compound 10 or 16 used according to the invention are added in diethylcarbonate. As the oil forming agent, 100 g of a 50% solution (in diethylcarbonate) is added of the compound

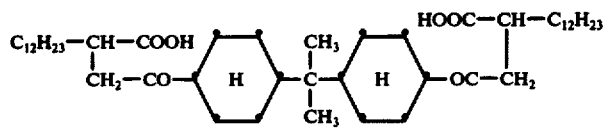

and 85 g of a 30% methanolic solution of the compound

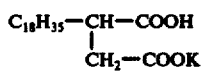

This mixture is emulsified at 50° C in 1000 ml of a 10% gelatine solution with an intensive stirrer.

The solvent is removed in a thin layer evaporator and the emulsion obtained is stored at 4° C.

2. Yellow Coupler Emulsion 5 g sulphosuccinic acid-bis-(2-ethyl-hexyl)-ester, followed by 50 g yellow coupler of the following constitution are dissolved in 200 g diethylcarbonate at 40° C

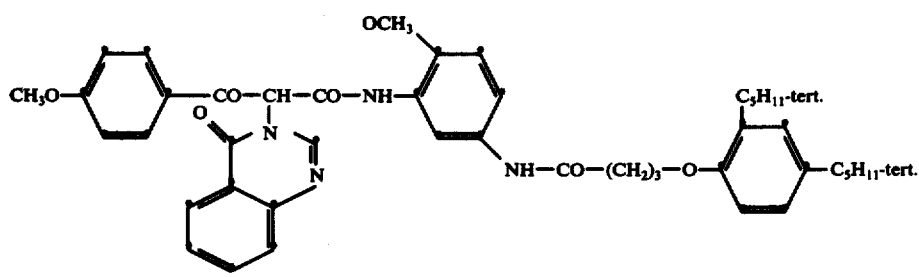

Subsequently 50 g of a 50% solution of compounds 10 or 16 according to the invention are added in diethylcarbonate. As oil forming agents 50 g of a 50% solution (in diethylcarbonate) of the compound:

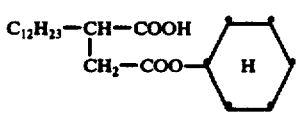

and 25 g dibutylphthalate are added. This mixture is emulsified at 50° C in 1000 ml of a 10% gelatine. The solvent is removed in a thin layer evaporator and the emulsion obtained is stored at 4° C.

3. Cyan Coupler Emulsion 5 g sulphosuccinic acid-bis-(2-ethyl-hexyl)-ester followed by 35 g cyan coupler of the following constitution are dissolved in 175 g diethylcarbonate at 40° C:

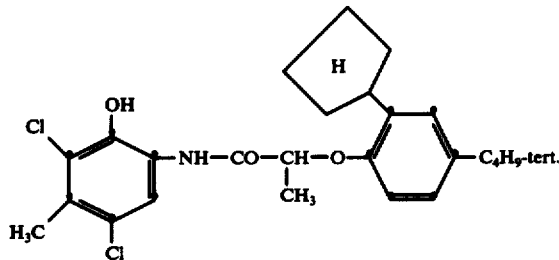

Subsequently 70 g of a 50% solution of compound 10 or 16 in diethylcarbonate are added. As the oil forming agents 70 g of a 50% solution (in diethylcarbonate) of the compound

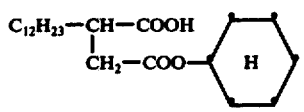

and 60 g of a 30% methanolic solution of the compound

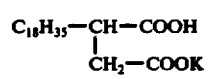

are added. This mixture is emulsified at 50° C in 1000 ml of a 10% gelatine. The solvent is removed in a thin layer evaporator and the emulsion thus obtained is stored at 4° C.

II. Production of a colour recording material

A colour recording material is produced by applying the following layers one after another on a paper-backing coated with polyethylene and provided with an adhesive layer, with the emulsion layers containing the conventional additives of wetting agents, stabilisers etc:

1. As the undercoat layer a 4 μ thick blue sensitive silver bromide emulsion layer, which contains per kilogram of emulsion 25.4 g silver (88% AgBr, 12% AgCl), 80 g gelatine and 34 g of the yellow coupler of the following formula:

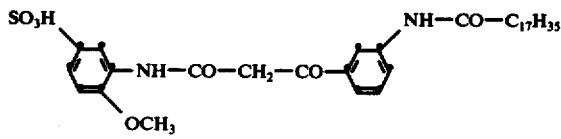

2. As the intermediate layer a 1μ thick gelatine layer,
3. As the middle coat a 4 μ thick green-sensitive silver chloride bromide emulsion layer, which contains per kilogram of emulsion 22 g silver (77% silver chloride, 23% silver bromide), 80 g gelatine and 650 g of the magenta coupler emulsion described in I.1.
4. A 4μ thick ultraviolet protection layer which contains per square meter 0.7 g ultraviolet absorber of the composition

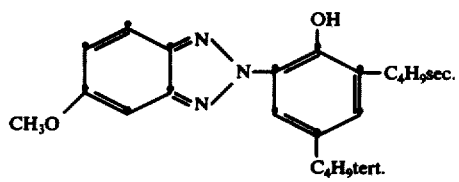

5. As the top coat a 4μ thick red sensitive silver chloride bromine emulsion layer which contains per kilogram of emulsion 23 g silver (80% silver chloride, 20% silver bromide), 80 g gelatine and 15.6 g of the cyan coupler

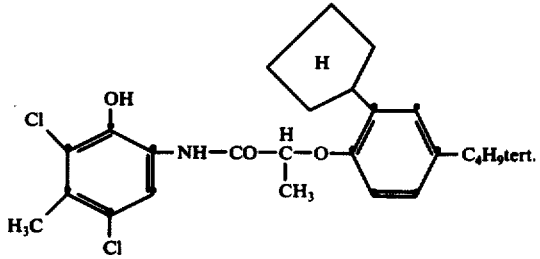

6. A 1μ thick gelatine layer.

III. 1) Use in the Magenta Layer

Stability Comparison

To test the effectiveness of the compounds according to the invention, a colour recording material as described under II was prepared. In a comparative material a coupler emulsion was used in the green-sensitive layer having the same composition as the magenta coupler emulsion described under I.1, with the one exception that none of the compounds according to the invention was used. The comparison was conducted in such a way that in each case in the materials -which were exposed in a conventional sensitometer behind a neutral grey step wedge or behind a continuous tone colour separation wedge, were subsequently colour developed, bleached, fixed and washed in the usual manner- a point with a magenta density of 0.7 was ascertained and identified. The materials were then exposed to daylight at $7.5 \times 10^6$ lux.h in an exposure position facing south in 60% relative humidity. Subsequently, by measuring at the same point, the colour decrease was determined.

| a) | Decrease of color density in the grey wedge | |
|---|---|---|
| | without the addition of the compounds according to the invention | - 55% |
| | addition of compound 10 | - 25% |
| | addition of compound 16 | - 24% |
| b) | Decrease in separation wedge | |
| | without the addition of the compounds according to the invention | - 78% |
| | addition of compound 10 | - 29% |
| | addition of compound 16 | - 31% |

In a further series of tests, coupler emulsions products were produced as described in I.1, with the difference that 0.25 or 1 parts by weight of the compounds according to the invention, and not 0.5 parts, were used per 1 part by weight of colour coupler. The colour recording materials were produced as under II. The following values were obtained upon exposure.

| Decrease in the grey wedge | |
|---|---|
| without the addition of the compounds according to the invention | - 56% |
| addition of 0.25 parts of compound 10 | - 31% |
| addition of 1 part of compound 10 | - 20% |
| addition of 0.25 parts of compound 16 | - 29% |
| addition of 1 part of compound 16 | - 19% |
| Decrease in color separation | |
| without addition of compounds according to the invention | - 81% |
| addition of 0.25 parts of the compounds | - 36% |
| addition of 1 part of compound 10 | - 25% |
| addition of 0.25 parts of compound 16 | - 38% |
| addition of 1 part of compound 16 | - 27% |

2. Use in the yellow layer

With the colour material described under II instead of the alkali soluble yellow coupler, 860 g of the yellow coupler emulsion described in I.2 are added in the undercoat and the light stability is determined.

| a) | Decrease in the grey wedge | |
|---|---|---|
| | without addition of the compounds according to the invention | - 41% |
| | addition of compound 10 | - 25% |
| | addition of compound 16 | - 21% |
| b) | Decrease in color separation | |
| | without addition of the compounds according to the invention | - 55% |
| | addition of compound 10 | - 34% |
| | addition of compound 16 | - 29% |

In a further test, in the coupler emulsion described under I.2, instead of 0.5 parts, 1 part of the compound according to the invention is used and the light stability is determined.

| a) | Decrease in the grey wedge |
|---|---|

-continued

|   |   |   |
|---|---|---|
| | without addition of the compounds according to the invention | - 42% |
| | addition of one part of compound 16 | - 18% |
| b) | Decrease in separation wedge | |
| | without addition of the compounds according to the invention | - 57% |
| | addition of one part of compound 16 | - 24% |

3. Use in the cyan layer

In the colour material described under II, 640 g of the cyan coupler emulsion described under I.3 are added and the light stability is determined.

As the cyan dye is unprotected in the uppermost layer, the decrease in the grey wedge corresponds to the decrease in the colour separation.

| Decrease in the color separation | |
|---|---|
| without addition of the compounds according to the invention | - 31% |
| addition of compound 10 | - 16% |
| addition of compound 16 | - 14% |

IV Influence of the oil forming agent

A comparison was conducted with the oil forming agents described in I according to U.S. Pat. No. 3,689,271 firstly, and dibutylphthalate, according to U.S. Pat. No. 2,322,027 secondly, with in each case the magenta coupler described in I.1 being used. The tests were coated as magenta single layers and exposed at 5 × 10⁶lux.h to a Xenon lamp.

| b) | | |
|---|---|---|
| With the ultraviolet protective layer and with the addition of compound number 10 according to the invention measured at d = 0.7. | | |
| test with oil forming agents as under I: | | - 14% |
| test with dibutylphthalate: | | - 39% |

By the addition of the oil forming agents mentioned in I, the heavy greying of the image whites was reduced.

| tests with oil forming agents as in I: | | - 58% |
|---|---|---|
| tests with dibutylphthalate: | | - 62% |
| Image whites after exposure | | |
| tests with oil forming agents as in I: | yellow | 0.12 |
| | magenta | 0.11 |
| | cyan | 0.21 |
| tests with dibutylphthalate: | yellow | 0.27 |
| | magenta | 0.22 |
| | cyan | 0.21 |

The effect of the compounds according to the invention can be increased by the addition of the oil forming agents under I.

The stated values were obtained when the material was developed with a colour developer bath, which as the colour developer contained a compound of the following formula:

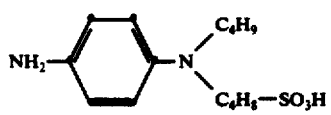

Within the limit of error, similar results are obtained with a colour developer of the following formula:

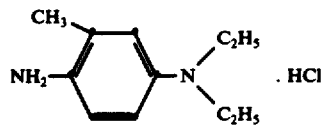

We claim:

1. A light sensitive color photographic material capable of providing dye images upon exposure and development in a conventional liquid color developer and having improved resistance to bleaching of the dye image containing a silver halide emulsion and at least one hydrophilic binder layer containing a color coupler for the production of a dye image and in said binder layer in an amount to effectively reduce the bleaching of the produced dye image a hydroxy indane of the following formula:

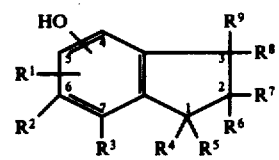

in which $R^1$ = hydrogen, alkyl, cycloalkyl, aralkyl or a further hydroxy indane radical bonded by —S—, —SO₂—, —O—, or a straight or branched chain alkylene bridge, of the formula:

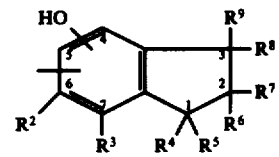

$R^2$ & $R^3$ = hydrogen, halogen, —NO₂, carboxyl, alkyl, cycloalkyl, aralkyl, aryl, where the stated alkyl, cycloalkyl, aralkyl and aryl groups can contain further substituents; $R_2$ and $R_3$ together can represent the radical necessary for completing a condensed carbocyclic ring;

$R^4$ & $R^5$ = hydrogen, alkyl, cycloalkyl, aryl, or $R^4$ and $R^5$ together can represent the radical necessary for completing a 5- or 6-membered cycloaliphatic ring;

$R^6$ and $R^7$ = hydrogen, alkyl, cycloalkyl, aralkyl or phenyl; $R^6$ and $R^7$ together can represent the radical necessary for completing a 5- or 6-membered cycloaliphatic ring;

$R^8$ and $R^9$ = as $R^6$ and $R^7$; when $R^8$ and $R^9$ together represent the radical necessary for completing a 5- or 6-membered carbocyclic ring which may contain an annulated ring, this radical when annulated can contain a hydroxyl subtituted benzo ring, capable of forming a dihydroxyspiro-bis-indane.

2. A photographic material according to claim 1, wherein $R^1$ represents hydrogen in the 4-position, $R^2$ represents hydrogen or alkyl with up to 12 carbon atoms, $R^3$, $R^6$ and $R^7$ each represent hydrogen and $R^4$, $R^5$, $R^8$ each represent hydrogen or methyl.

3. A photographic material according to claim 1, wherein it additionally contains a compound of the following formula:

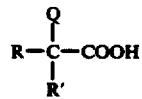

wherein

R = A saturated or olefinically unsaturated, aliphatic hydrocarbon group with 1 to 18 carbon atoms, R' = hydrogen or a saturated or olefinically unsaturated aliphatic hydrocarbon group with 1 to 18 carbon atoms, which may be substituted, Q = —COX or -CH$_2$COX, where X can represent:
b 1. H, OH, alkoxy
2. the group —O-alkylene-[O-alkylene]$_n$-O-alkyl, in which $n$ = 0 to 10,
3. an amino,
4. hydrazino or
5. hydroxylamino group.

* * * * *